(12) United States Patent
Deevi et al.

(10) Patent No.: US 9,996,745 B2
(45) Date of Patent: Jun. 12, 2018

(54) BLENDING OF AGRICULTURAL PRODUCTS VIA HYPERSPECTRAL IMAGING AND ANALYSIS

(71) Applicant: ALTRIA CLIENT SERVICES INC., Richmond, VA (US)

(72) Inventors: Seetharama C. Deevi, Midlothian, VA (US); Henry M. Dante, Midlothian, VA (US); Qiwei Liang, Midlothian, VA (US); Samuel Timothy Henry, Midlothian, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 833 days.

(21) Appl. No.: 14/084,213

(22) Filed: Nov. 19, 2013

(65) Prior Publication Data

US 2014/0137877 A1    May 22, 2014

Related U.S. Application Data

(60) Provisional application No. 61/728,123, filed on Nov. 19, 2012.

(51) Int. Cl.
*G06K 9/00* (2006.01)
*G06K 9/46* (2006.01)
(Continued)

(52) U.S. Cl.
CPC .............. *G06K 9/0063* (2013.01); *A24B 3/16* (2013.01); *A24B 15/18* (2013.01); *B07C 5/342* (2013.01);
(Continued)

(58) Field of Classification Search
USPC ............. 382/191, 110; 250/339.07; 256/451; 131/290
See application file for complete search history.

(56) References Cited

U.S. PATENT DOCUMENTS 3,854,586 A    12/1974 Perkins
3,939,983 A    2/1976 Asfour
(Continued)

FOREIGN PATENT DOCUMENTS

CN    101627832    1/2010
WO    0058035 A1    10/2000
(Continued)

OTHER PUBLICATIONS

International Search Report of International Application No. PCT/US2013/070809 dated Mar. 7, 2014.
(Continued)

*Primary Examiner* — Kathleen Y Dulaney
(74) *Attorney, Agent, or Firm* — Roberts Mlotkowski Safran Cole & Calderon, P.C.

(57) ABSTRACT

Provided is a method for blending of agricultural product utilizing hyperspectral imaging. At least one region along a sample of agricultural product is scanned using at least one light source of different wavelengths. Hyperspectral images are generated from the at least one region. A spectral fingerprint for the sample of agricultural product is formed from the hyperspectral images. A plurality of samples of agricultural product is blended based on the spectral fingerprints of the samples according to parameters determined by executing a blending algorithm.

14 Claims, 6 Drawing Sheets

(51) Int. Cl.

| | | |
|---|---|---|
| *G01J 3/45* | (2006.01) | |
| *G01J 5/02* | (2006.01) | |
| *A24B 3/10* | (2006.01) | |
| *G01J 3/28* | (2006.01) | |
| *A24B 15/18* | (2006.01) | |
| *G06K 9/62* | (2006.01) | |
| *G01N 21/31* | (2006.01) | |
| *A24B 3/16* | (2006.01) | |
| *B07C 5/342* | (2006.01) | |
| *B07C 5/36* | (2006.01) | |
| *G06F 17/30* | (2006.01) | |
| *G06T 7/00* | (2017.01) | |
| *G01N 21/84* | (2006.01) | |

(52) U.S. Cl.
CPC ............... *B07C 5/366* (2013.01); *G01J 3/28* (2013.01); *G01J 3/2823* (2013.01); *G01N 21/31* (2013.01); *G01N 21/84* (2013.01); *G06F 17/3028* (2013.01); *G06K 9/4604* (2013.01); *G06K 9/6202* (2013.01); *G06T 7/0008* (2013.01); *G01J 2003/2826* (2013.01); *G01N 2021/8461* (2013.01); *G01N 2021/8466* (2013.01); *G06K 2009/4657* (2013.01); *G06T 2207/20024* (2013.01); *G06T 2207/30108* (2013.01); *G06T 2207/30188* (2013.01)

(56) References Cited

U.S. PATENT DOCUMENTS

| | | | |
|---|---|---|---|
| 4,018,674 A | | 4/1977 | Morris |
| 4,296,405 A | * | 10/1981 | Rich ........................ A24C 1/04 131/105 |
| 4,528,993 A | | 7/1985 | Sensabaugh et al. |
| 4,609,108 A | | 9/1986 | Hristozov et al. |
| 4,624,269 A | | 11/1986 | Story et al. |
| 4,778,987 A | | 10/1988 | Saaski et al. |
| 4,836,224 A | | 6/1989 | Lawson et al. |
| 4,924,883 A | | 5/1990 | Perfetii et al. |
| 4,924,888 A | | 5/1990 | Perfetii et al. |
| 4,987,907 A | | 1/1991 | Townend |
| 5,056,537 A | | 10/1991 | Brown et al. |
| 5,085,325 A | | 2/1992 | Jones et al. |
| 5,092,352 A | | 3/1992 | Sprinkle |
| 5,159,942 A | | 11/1992 | Brinkley et al. |
| 5,220,930 A | | 6/1993 | Gentry |
| 5,301,694 A | | 4/1994 | Raymond et al. |
| 5,360,023 A | | 11/1994 | Blakley et al. |
| 5,360,024 A | | 11/1994 | Greig |
| 5,387,416 A | | 2/1995 | White |
| 5,476,108 A | | 12/1995 | Dominguez et al. |
| 5,972,404 A | * | 10/1999 | van Lengerich ......... A21D 2/16 426/496 |
| 6,400,833 B1 | | 6/2002 | Richert |
| 6,421,126 B1 | | 7/2002 | Kida et al. |
| 6,438,261 B1 | * | 8/2002 | Moshe ............... G01N 15/1475 382/133 |
| 6,490,035 B1 | * | 12/2002 | Folestad ................. B01F 15/04 356/301 |
| 6,517,230 B1 | * | 2/2003 | Afnan ................. B01F 7/00908 366/142 |
| 6,587,575 B1 | * | 7/2003 | Windham ............. G01N 21/31 250/458.1 |
| 6,646,264 B1 | * | 11/2003 | Modiano ............. G01N 21/359 250/339.07 |
| 6,701,936 B2 | | 3/2004 | Shafer et al. |
| 6,730,832 B1 | | 5/2004 | Dominguez et al. |
| 6,819,798 B2 | | 11/2004 | Gorin |
| 6,953,040 B2 | | 10/2005 | Atchley et al. |
| 7,032,601 B2 | | 4/2006 | Atchley et al. |
| 7,142,988 B1 | | 11/2006 | Johnson |
| 7,335,847 B2 | | 2/2008 | Drewes et al. |
| 7,383,840 B2 | | 6/2008 | Coleman |
| 7,411,682 B2 | | 8/2008 | Moshe |
| 7,450,761 B2 | | 11/2008 | Portigal et al. |
| 7,518,710 B2 | | 4/2009 | Gao et al. |
| 7,812,939 B2 | * | 10/2010 | Merrill, II .............. B01F 9/02 356/73 |
| 8,564,769 B2 | | 10/2013 | Zou et al. |
| 8,775,219 B2 | | 7/2014 | Swanson et al. |
| 8,953,158 B2 | * | 2/2015 | Moshe ................. B07C 5/3422 356/300 |
| 8,967,851 B1 | * | 3/2015 | Kemeny ............. B01F 7/00908 366/142 |
| 2001/0000386 A1 | | 4/2001 | Peele |
| 2002/0008055 A1 | | 1/2002 | Campbell et al. |
| 2003/0075193 A1 | | 4/2003 | Li et al. |
| 2003/0131859 A1 | | 7/2003 | Li et al. |
| 2004/0084056 A1 | | 5/2004 | Lawson et al. |
| 2004/0135086 A1 | * | 7/2004 | Lewis ..................... G01N 1/06 250/339.12 |
| 2004/0255965 A1 | | 12/2004 | Perfetii et al. |
| 2005/0057263 A1 | | 3/2005 | Moshe et al. |
| 2005/0066984 A1 | | 3/2005 | Crooks et al. |
| 2005/0066986 A1 | | 3/2005 | Nestor et al. |
| 2005/0244521 A1 | | 11/2005 | Strickland et al. |
| 2006/0292246 A1 | * | 12/2006 | Wu ..................... G01N 30/8675 424/725 |
| 2008/0245377 A1 | | 10/2008 | Marshall et al. |
| 2009/0171591 A1 | | 7/2009 | Timmis et al. |
| 2009/0293889 A1 | | 12/2009 | Kumar et al. |
| 2011/0125477 A1 | | 5/2011 | Lightner et al. |
| 2012/0250025 A1 | * | 10/2012 | Moshe ................. B07C 5/3422 356/451 |
| 2012/0290223 A1 | * | 11/2012 | Mertens ................. G01J 3/28 702/25 |
| 2012/0321759 A1 | * | 12/2012 | Marinkovich ....... A61B 5/0531 426/231 |
| 2013/0022250 A1 | | 1/2013 | Nygaard et al. |
| 2013/0229516 A1 | * | 9/2013 | Jones ..................... G01N 21/35 348/143 |
| 2014/0236359 A1 | * | 8/2014 | Minvielle ............. G01N 33/02 700/275 |
| 2015/0044098 A1 | | 2/2015 | Smart et al. |
| 2015/0283586 A1 | | 10/2015 | Dante et al. |

FOREIGN PATENT DOCUMENTS

| | | |
|---|---|---|
| WO | WO0237990 A2 | 5/2002 |
| WO | 2004/095959 A1 | 11/2004 |
| WO | 2005/016036 A1 | 2/2005 |
| WO | 2005/041699 A2 | 5/2005 |
| WO | 2005/063060 A1 | 7/2005 |
| WO | 2007041755 A1 | 4/2007 |
| WO | 2007099540 A1 | 9/2007 |
| WO | 2011027315 A1 | 3/2011 |
| WO | 2014078858 | 5/2014 |
| WO | 2014078861 | 5/2014 |
| WO | 2014078862 | 5/2014 |

OTHER PUBLICATIONS

Pilar Beatriz Garice-Allende, "Hyperspectral Imaging Sustains Production-Process Competitiveness", Spie Newsroom, Jan. 1, 2010, DOI:10.11172.1201003.002681.

Timothy Kelman et al., "Classification of Chinese Tea Samples for Food Quality Control Using Hyperspectral Imaging", Hyperspectral Imaging Conference, Jan. 1, 2011.

International Search Report of International Application No. PCT/US2013/070812 dated Mar. 7, 2014.

Robin Gruna et al., "Hyperspectral Imaging—From Laboratory to In-line Food Sorting", Cigar Workshop on Image Analysis in Agriculture, Jan. 1, 2010.

Luis Rodriguez-Cobo et al., "Raw Material Classification by Means of Hyperspectral Imaging and Hierarchical Temporal Memories", IEEE Sensors Journal, IEEE Service Center, New York, NY, US, vol. 12, No. 9, Sep. 1, 2012, ISSN:1530-437X, DOI: 10.1109.2012.2202898.

(56) References Cited

OTHER PUBLICATIONS

P. Beatriz Garcia-Allende et al., "Hyperspectral Imaging for Diagnosis and Quality Control in Agri-food and Industrial Sectors,"Proceedings of SPIE:,vol. 7726, Apr. 30, 2011, ISSN: 0277-786X,DOI: 10.1117.12.744506.
International Search Report of International Application No. PCT/US2013/070814 dated Mar. 7, 2014.
Russ Ouellette, "The Basics of Tobacco and Blending", pipesmagaazine.com, Jul. 14, 2010, Retrieved from the Internet: URL: http://pipesmagazine.com/blog/put-that-in-your-pipe/the-basucs-of-tobacco-blending.
Browne, "The Design of Cigarettes", 3.sup.rd Ed., pp. 43 (1990).
International Preliminary Report on Patentability for International Patent Application No. PCT/US2013/070809 dated Nov. 19, 2013.
International Preliminary Report on Patentability for International Patent Application No. PCT/US2013/070812 dated Nov. 19, 2013.
International Preliminary Report on Patentability for International Patent Application No. PCT/US2013/070814 dated Nov. 19, 2013.
International Preliminary Report on Patentability for International Patent Application No. IPRP PCT/IB2010/053952 dated Mar. 6, 2012.
Garner, "Principles and Practical Methods of Curing Tobacco", USDA Bulletin No. 143, 7-54 (1909).
Darkis et al., "Flue-Cured Tobacco Correlation between Chemical Compositio and Stalk Position of Tobaccos Produced under Varying Weather Conditions", Industrial & Engineering Chemistry, 28 (10) 1214-1223 (1936).
Bacon et al., "Biochemical Changes in Tobacco During Flue Curing", USDA Tech. Bulletin No. 1032 (1951).
Darkis et al., "Cigarette Tobaccos. Chemical Changes that Occur during Processing" Industrial & Engineering Chemistry, 44 (2), 284-291 (1952).
Bacon et al., "Chemical Changes in Tobacco during Flue-Curing", Industrial & Engineering Chemistry, 44 (2), 292-309 (1952).
Davis et al., "Tobacco Production, Chemistry and Technology", Blackwell Science, pp. 346 and 440-451, (1999).
Voges, "Tobacco Encyclopedia", Tobacco Journal International, pp. 44-45 (1984).
Bombick et al. "Evaluation of the Genotoxic and Cytotoxic Potential of Mainstream Whole Smoke and Smoke Condensate from a Cigarette Containing a Novel Carbon Filter", Fundamental and Applied Toxicology, vol. 39, pp. 11-17 (1997).
Walker et al., "Curing Flue-Cured Tobacco in Canada", Publication 1312/E (1987).
Suggs et al., "Bulk Density and Drying Effect on Air Flow Through Flue-Cured Tobacco Leaves", Tobacco Scence yearbook, 33, 86-90 (1989).
Hawks, Jr., "Principles of Flue-Cured Tobacco Production", Second Edition (1978).
"Flue-Cured Tobacco Information", North Carolina Cooperative Extension Service, North Carolina State University, 1993.
Peele et al., "Impact of Plant Manipulation and Post Harvest Phenomena on Leaf Composition", Recent Advances in Tobacco Science, 21, 1-181 (1995).
Cooper et al., "Drying and Curing of Bright Leaf Tobacco by Means of Conditioned Air: Engineering Experiment Station Series" Bulletin of The Virginia Polytechnic Institute, 37(6), 3-28 (1939).
Brown et al., "Engineering Phases of Curing Bright Leaf Tobacco", Agriculture Engineering, 29(3), 109-111 (1948).
Johnson et al., "Bulk Curing of Bright Leaf Tobacco", Tobacco Science, 4, 49-55 (1960).
Johnson, "Production factors affecting chemical properties of the flue-cured leaf", Tobacco International 177(11): 12-19 (1975).
Davis et al., "Tobacco: Production, Chemistry and Technology", 1st Edition, pp. 131-133 (1999).
Legg et al., "40th Tobacco Chemists' Research Conference", Holiday Inn World's Fair (1986).

* cited by examiner

BLENDING OF AGRICULTURAL PRODUCTS VIA HYPERSPECTRAL IMAGING AND ANALYSIS

RELATED APPLICATION

This application claims the benefit of U.S. Provisional Application Ser. No. 61/728,123, filed on Nov. 19, 2012, the contents of which are hereby incorporated by reference in their entirety.

FIELD

Disclosed herein is a method and system for the blending of agricultural products, such as tobacco, using hyperspectral imaging and analysis. Embodiments disclosed herein can be practiced with other agricultural products, including but not limited to, tea, grapes, coffee, vegetables, fruit, nuts, breads, cereals, meat, fish and other plant or animal parts.

ENVIRONMENT

Certain agricultural products, such as cultivated tobacco plants tea, spinach, etc., are harvested for their leaves, which may then be dried and cured as in the case of tobacco or tea. In the manufacture of cigarettes and other tobacco products, blends of different types of tobaccos are frequently employed, with three main types of tobacco used in U.S. blends. These tobacco types are Virginia or flue-cured, Burley and Oriental. Similar blending of different varieties and qualities of tea leaves is also done. In the following, the method and the system are illustrated for application in the tobacco industry, though the same method and system could be used for other agricultural products using leaves like tea and spinach, or in other packaged agricultural products using fruits, grapes, tomatoes, and other vegetables.

Regarding tobacco leaves, Virginia, or flue-cured tobacco, is also called "bright tobacco" since it turns a bright yellow-orange color during curing. It grows particularly well in Georgia, Virginia and the Carolinas. Flue-curing is a heat driven process that reduces the risk of mold and promotes chemical changes that improve the sensory quality of the tobacco.

Burley tobacco is a slightly lighter green leaf than Virginia tobacco. It requires heavier soils and is grown in Maryland, Kentucky and elsewhere. After harvesting, Burley tobaccos are air cured to reduce the risk of mold and improve sensory quality. In contrast to flue-curing, for Burley tobacco, air-curing takes place under ambient conditions.

Oriental tobacco is the smallest and hardiest of all tobacco types, grown principally in the Balkans, Turkey and the Middle East. These conditions and a high planting density create an aromatic flavor. Oriental tobacco is typically sun-cured.

Typically, tobacco materials are used in blended form. For example, certain popular tobacco blends, commonly referred to as "American" blends, comprise mixtures of flue-cured tobacco, burley tobacco and Oriental tobacco. Such blends, in many cases, contain tobacco materials that have processed forms, such as processed tobacco stems (e.g., cut-rolled stems, cut-rolled-expanded stems or cut-puffed stems), volume expanded tobacco (e.g., puffed tobacco, such as dry ice expanded tobacco (DIET), preferably in cut filler form). Tobacco materials also can have the form of reconstituted tobaccos (e.g., reconstituted tobaccos manufactured using paper-making type or cast sheet type processes). Tobacco reconstitution processes traditionally convert portions of tobacco that normally might be wasted into commercially useful forms. For example, tobacco stems, recyclable pieces of tobacco and tobacco dust can be used to manufacture processed reconstituted tobaccos of fairly uniform consistency. See, for example, Tobacco Encyclopedia, Voges (Ed.) p. 44-45 (1984), Browne, The Design of Cigarettes, 3.sup.rd Ed., p. 43 (1990) and Tobacco Production, Chemistry and Technology, Davis et al. (Eds.) p. 346 (1999). Various representative tobacco types, processed types of tobaccos, types of tobacco blends, cigarette components and ingredients, and tobacco rod configurations, also are set forth in U.S. Pat. No. 4,836,224 to Lawson et al.; U.S. Pat. No. 4,924,883 to Perfetti et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,730,832 to Dominguez et al.; and U.S. Pat. No. 6,701,936 to Shafer et al.; U.S. Patent Application Publication Nos. 2003/0075193 to Li et al.; 2003/0131859 to Li et al.; 2004/0084056 to Lawson et al.; 2004/0255965 to Perfetti et al.; 2005/0066984 to Crooks et al.; and 2005/0066986 to Nestor et al.; PCT WO 02/37990 to Bereman; and Bombick et al., Fund. Appl. Toxicol., 39, p. 11-17 (1997); which are incorporated herein by reference.

Dark air-cured tobacco is a type of tobacco used mainly for chewing tobacco, snuff, cigars, and pipe blends. Most of the world production of such tobacco is confined to the tropics; however, sources of dark air-cured tobacco are also found in Kentucky, Tennessee, and Virginia. Dark air-cured tobacco plants are characterized by leaves with a relatively heavy body and such tobacco plants are typically highly fertilized and topped low to around 10-12 leaves. See Tobacco Production, Chemistry and Technology, Davis et al. (Eds.) pp. 440-451 (1999).

These tobacco types may be further broken down into subgroups which may depend upon where the tobacco is grown, which part of the plant it is taken from, weather conditions and other characteristics that relate to the quality of the tobacco, including aroma, color, maturity, and uniformity. It should be understood that similar situation prevails in other leafy vegetables, fruits and other agricultural produce as well.

One tobacco plant can produce leaves of varying properties. The sensory, physical, chemical and visual properties of a tobacco leaf are, to a large extent, but not wholly determined by the leaf position on the plant. For example, the leaves at the top of the plant have more exposure to the sun than the ones at the bottom and typically contain higher levels of compounds that are sensorially important. In addition, the chemical content of the leaf can vary widely depending on the type of tobacco, soil, environmental, prevailing weather conditions, where it was grown, the way it is cured and how it is matured.

As in the case of any agricultural product, tobacco may be characterized by a wide variety of physical, chemical, and/or biological properties, characteristics, features, and behavior, which are associated with various aspects relating to agriculture, agronomy, horticulture, botany, environment, geography, climate, and ecology of the tobacco crop and plants thereof from which tobacco leaves are derived. Moreover, these properties of tobacco leaves may be spatially (i.e., geographically) and temporally (i.e., seasonally) variable or dependent. Such definition and characterization of tobacco leaves are directly translatable and extendable to defining and characterizing tobacco samples.

The forms disclosed herein are generally focused on the domains encompassing blending of tobacco bales, and are specifically focused on the domains encompassing automatic blending of tobacco that can be performed via hyperspectral imaging and analysis. However, it will be appreciated by those skilled in the art that the technique could be used for applications involving other agricultural products, including, but not limited to, tea, spinach, fruits, vegetables, etc.

In the general technique of hyperspectral imaging, one or more objects in a scene or sample are affected in a way, such as excitation by incident electromagnetic radiation supplied by an external source of electromagnetic radiation upon the objects, which causes each object to reflect, scatter and/or emit electromagnetic radiation featuring a spectrum.

Hyperspectral imaging and analysis is a combined spectroscopy and imaging type of analytical method involving the sciences and technologies of spectroscopy and imaging. By definition, hyperspectral imaging and analysis is based on a combination of spectroscopy and imaging theories, which are exploitable for analyzing samples of physical, chemical, and/or biological matter in a highly unique, specialized, and sophisticated, manner.

Hyperspectral images generated by and collected from a sample of matter may be processed and analyzed by using automatic pattern recognition and/or classification type data and information processing and analysis, for identifying, characterizing, and/or classifying, the physical, chemical, and/or biological properties of the hyperspectrally imaged objects in the sample of matter.

There remains a need for a method and system for automatic quality evaluation and blending agricultural products, such as tobacco, via hyperspectral imaging and analysis.

SUMMARY

Disclosed herein is a method and system for quality evaluation and blending of agricultural products, including tobacco, via hyperspectral imaging and analysis. The method and system disclosed herein provide high sensitivity, high resolution, and high speed during operation, in a simple yet highly efficient, cost effective and commercially applicable manner.

In one aspect, disclosed herein is a method for blending of agricultural product utilizing hyperspectral imaging. At least one region along a sample of agricultural product is scanned using at least one light source of appropriate spectral wavelengths. Hyperspectral images are generated from the at least one region. A spectral fingerprint for the sample of agricultural product is formed from the hyperspectral images. A plurality of samples of agricultural product is blended based on the spectral fingerprints of the samples according to parameters determined by a computer, based upon an intelligent algorithm devised for the application.

In another aspect, provided is a method for determining blending parameters for an agricultural product utilizing hyperspectral imaging. Multiple regions along a sample of a desirable agricultural product are scanned using at least one light source of appropriate spectral wavelengths. Hyperspectral images are generated from the multiple regions. A spectral fingerprint is formed for the sample from the hyperspectral images. One or more features of the spectral fingerprint are correlated to desirable sensory attributes of the sample.

Certain forms disclosed herein are focused on the domain encompassing the testing of agricultural products, including tobacco bales, lots or samples, based on measuring, analyzing, and determining micro scale properties, characteristics, features, and parameters, generally with respect to individual bales, lots or samples, and specifically with respect to individual leaves contained within the bales, lots or samples. A wide variety of physical, chemical, and/or biological properties may be determined. Blending of agricultural products, including tobacco, is provided. Certain forms disclosed herein may be performed in an automatic on-line manner, via hyperspectral imaging and analysis.

Certain forms disclosed herein include definition and use of hyperspectrally detectable and classifiable codes. In turn, the classified agricultural product such as tobacco contained within that particular tobacco bale, lot or sample is usable as part of a procedure for blending that particular tobacco bale, lot or sample.

Certain forms disclosed herein provide for tracking and accounting for the spatial (i.e., geographical) and temporal (i.e., seasonal) variability of physical, chemical, and/or biological properties and behavior of agricultural product such as tobacco leaves. Such spatial and temporal variability or dependency of agricultural product such as tobacco leaves can be uniquely tracked and accounted for by use of the hyperspectrally detectable and classifiable codes and can therefore be incorporated into a procedure for blending tobacco.

Certain forms disclosed herein are implemented according to a temporal gated type of hyperspectral imaging and analysis. Accordingly, in some forms thereof, a method and system for the blending of agricultural product such as tobacco via temporal gated hyperspectral imaging and analysis is provided.

Certain forms disclosed herein are implemented by performing steps or procedures, and sub-steps or sub-procedures, in a manner selected from the group consisting of manually, semi-automatically, fully automatically, and combinations thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular form, the steps or procedures, and sub-steps or sub-procedures are performed by using hardware, software, and/or an integrated combination thereof, and the system units, sub-units, devices, assemblies, sub-assemblies, mechanisms, structures, components, and elements, and peripheral equipment, utilities, accessories, and materials, operate by using hardware, software, and/or an integrated combination thereof.

For example, software used, via an operating system, for implementing certain forms disclosed herein can include operatively interfaced, integrated, connected, and/or functioning written and/or printed data, in the form of software programs, software routines, software subroutines, software symbolic languages, software code, software instructions or protocols, software algorithms, or a combination thereof. For example, hardware used for implementing certain forms disclosed herein can include operatively interfaced, integrated, connected, and/or functioning electrical, electronic and/or electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital and/or analog operations. Certain forms disclosed herein can be implemented by using an integrated combination of the just described exemplary software and hardware.

In certain forms disclosed herein, steps or procedures, and sub-steps or sub-procedures can be performed by a data processor, such as a computing platform, for executing a plurality of instructions. Optionally, the data processor includes volatile memory for storing instructions and/or data, and/or includes non-volatile storage, for example, a magnetic hard-disk and/or removable media, for storing instructions and/or data. Optionally, certain forms disclosed herein include a network connection. Optionally, certain forms disclosed herein include a display device and a user input device, such as a touch screen device, keyboard and/or mouse.

BRIEF DESCRIPTION OF THE DRAWINGS

The forms disclosed herein are illustrated by way of example, and not by way of limitation, for the case of blending tobacco while manufacturing tobacco products in the figures of the accompanying drawings and in which like reference numerals refer to similar elements and in which.

DETAILED DESCRIPTION

Figure 1:
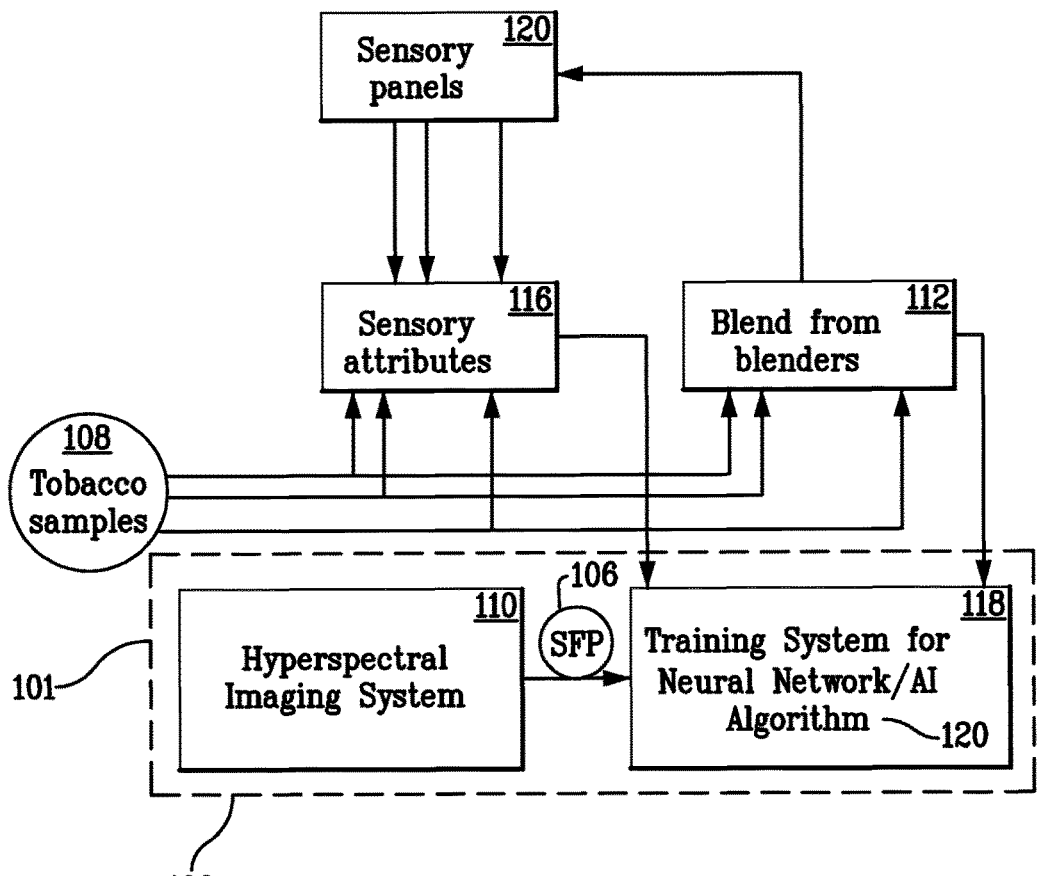
FIG. 1 presents, in block diagram form, a first stage of an automatic blending system, in accordance herewith.

Various aspects will now be described with reference to specific forms selected for purposes of illustration. It will be appreciated by those skilled in the art that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-6, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways, as can be appreciated by those skilled in the art.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Moreover, all technical and scientific words, terms, and/or phrases, introduced, defined, described, and/or exemplified, in the above sections, are equally or similarly applicable in the illustrative description, examples and appended claims.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary forms, alternative forms, specific configurations, and, additional and optional aspects, characteristics, or features, thereof, of the methods, and of the systems, disclosed herein, are better understood with reference to the following illustrative description and accompanying drawings. Throughout the following illustrative description and accompanying drawings, same reference notation and terminology (i.e., numbers, letters, and/or symbols), refer to same system units, system sub-units, devices, assemblies, sub-assemblies, mechanisms, structures, components, elements, and configurations, and, peripheral equipment, utilities, accessories, and materials, components, elements, and/or parameters.

As a means of illustration, the system will be described for application during tobacco processing and product development, but substantially the same system could be applied during the processing and product development of other agricultural products. Tobacco is packaged in the form of tobacco bales, graded and purchased from growers. A tobacco bale is a large, substantially rectangular shaped package of tobacco leaves and stems, tightly bound with a strong cord or wire or loosely packed in boxes. A typical Burley or Virginia tobacco bale may have dimensions on the order of at least about 1.2 meters per side and a corresponding volume on the order of about 1.7 cubic meters.

In a general manner, testing of tobacco samples may be divided into two major aspects: a macro scale aspect, and a micro scale aspect, where these two major aspects relate to different types of properties, characteristics, features, and parameters of tobacco.

The first major aspect is associated with macro scale properties of tobacco generally with respect to whole individual tobacco bales or lots, but not specifically with respect to single or individual tobacco leaves contained within the tobacco bales or lots. Primary examples of macro scale testing include weight of individual tobacco bales; physical size dimensions of individual tobacco bales; packing density of individual tobacco bales; void volume of individual tobacco bales; and moisture (water) content or humidity of individual tobacco bales or lots.

The second major aspect is associated with micro scale properties of tobacco, also generally with respect to individual tobacco bales or lots, but specifically with respect to individual tobacco leaves contained within the tobacco bales or lots, and more specifically with respect to a wide variety of numerous possible physical, chemical, and/or biological properties, characteristics, features, and parameters, of single or individual tobacco leaves contained within a given tobacco bale or lot.

Primary examples of such micro scale testing include physical shape and size dimensions of individual tobacco leaves; coloring of individual tobacco leaves; moisture (water) content of individual tobacco leaves; types, distribution, and composition of organic and inorganic chemical species or components of single or individual tobacco leaves; types, distribution, and composition of possible unknown or foreign matter or species on and/or within individual tobacco leaves; the behavior (activity and/or reactivity) of single or individual tobacco leaves in response to physical stimuli or effects, such as exposure to electromagnetic radiation; activity and/or reactivity of single or individual tobacco leaves in response to chemical stimuli or effects (such as exposure to aqueous liquids or to nonaqueous liquids; and activity and/or reactivity of individual tobacco leaves in response to biological stimuli or effects, such as exposure to biological organisms.

Ordinarily, it may be expected that the two major aspects or components of tobacco bale, lot or sample testing are essentially independent or separate from each other. However, depending upon (1) the particular macro scale and micro scale properties, characteristics, features, and parameters of the tobacco, and, depending upon (2) the particular properties, characteristics, features, and behavior of individual tobacco leaves contained within the tobacco bales, lots or samples, and depending upon (3) the particular context of tobacco bale, lot or sample testing, then, one major aspect may influence another major aspect.

The forms disclosed herein are generally focused on the domains encompassing blending of tobacco lots, blend components or samples, and are specifically focused on the domains encompassing automatic blending of tobacco lots or samples that can be performed via hyperspectral imaging and analysis. However, it should be understood that the forms disclosed herein could be applied to other domains encompassing blending of e.g. tea, fruits during the production of fruit juices, grapes for the production of wines as well as a vast array of other agricultural products.

As may be appreciated, the systems and methods described herein have multiple utilities. With regard to tobacco processing, in one form, blend components from different lots of tobacco (i.e., different harvest years, different locations, different weather conditions, etc.) may be blended to achieve desired attributes for that variety's use as a blending component. In another form, different blend components (i.e., different varieties) may be blended to produce a final blended tobacco, such as for a cut filler to be used to produce a particular brand of cigarette, cigar or smokeless product. For purposes of example, and not of limitation, a particular brand of cigarette could generally comprise twice the amount of Burley tobacco to flue cured, but be adjusted to provide the same sensory experience using the information revealed by the systems and methods described herein.

In hyperspectral imaging, a field of view of a sample is scanned and imaged while the sample is exposed to electromagnetic radiation. During the hyperspectral scanning and imaging there is generated and collected relatively large numbers of multiple spectral images, one-at-a-time, but, in an extremely fast sequential manner of the objects emitting electromagnetic radiation at a plurality of wavelengths and frequencies, where the wavelengths and frequencies are associated with different selected portions or bands of an entire hyperspectrum emitted by the objects. A hyperspectral imaging and analysis system can be operated in an extremely rapid manner for providing exceptionally highly resolved spectral and spatial data and information of an imaged sample of matter, with high accuracy and high precision, which are fundamentally unattainable by using standard spectral imaging and analysis.

In general, when electromagnetic radiation in the form of light, such as that used during hyperspectral imaging, is incident upon an object, the electromagnetic radiation is affected by one or more of the physical, chemical, and/or biological species or components making up the object, by any combination of electromagnetic radiation absorption, diffusion, reflection, diffraction, scattering, and/or transmission, mechanisms. Moreover, an object whose composition includes organic chemical species or components, ordinarily exhibits some degree of fluorescent and/or phosphorescent properties, when illuminated by some type of electromagnetic radiation or light, such as ultra-violet (UV), visible (VIS), or infrared (IR), types of light. The affected electromagnetic radiation, in the form of diffused, reflected, diffracted, scattered, and/or transmitted, electromagnetic radiation emitted by the object is directly and uniquely related to the physical, chemical, and/or biological properties of the object, in general, and of the chemical species or components making up the object, in particular, and therefore represents a unique spectral fingerprint or signature pattern type of identification and characterization of the object.

A typical spectral imaging system consists of an automated measurement system and analysis software. The automated measurement system includes optics, mechanics, electronics, and peripheral hardware and software, for irradiating, typically using an illuminating source, a scene or sample, followed by measuring and collecting light emitted, for example, by fluorescence, from objects in the scene or sample, and for applying calibration techniques best suited for extracting desired results from the measurements. Analysis software includes software and mathematical algorithms for analyzing, displaying, and presenting, useful results about the objects in the scene or sample in a meaningful way.

The hyperspectral image of a scene or a sample could be obtained from commercially available hyperspectral imaging cameras from Surface Optics Corporation of San Diego, Calif., among others, or custom built according to the user needs.

Each spectral image is a three dimensional data set of voxels (volume of pixels) in which two dimensions are spatial coordinates or position, (x, y), in an object and the third dimension is the wavelength, ($\lambda$), of the emitted light of the object, such that coordinates of each voxel in a spectral image may be represented as (x, y, $\lambda$). Any particular wavelength, ($\lambda$), of imaged light of the object is associated with a set of spectral images each featuring spectral fingerprints of the object in two dimensions, for example, along the x and y directions, whereby voxels having that value of wavelength constitute the pixels of a monochromatic image of the object at that wavelength. Each spectral image, featuring a range of wavelengths of imaged light of the object is analyzed to produce a two dimensional map of one or more physicochemical properties, for example, geometrical shape, form, or configuration, and dimensions, and/or chemical composition, of the object and/or of components of the object, in a scene or sample.

In hyperspectral imaging, multiple images of each object are generated from object emitted electromagnetic radiation having wavelengths and frequencies associated with different selected parts or bands of an entire spectrum emitted by the object. For example, hyperspectral images of an object are generated from object emitted electromagnetic radiation having wavelengths and frequencies associated with one or more of the following bands of an entire spectrum emitted by the object: the visible band, spanning the wavelength range of about 400-700 nanometers, the infra-red band, spanning the wavelength range of about 700-3000 nanometers, and the deep infra-red band, spanning the wavelength range of about 3-12 microns. If proper wavelengths and wavelength ranges are used during hyperspectral imaging, data and information of the hyperspectral images could be optimally used for detecting and analyzing by identifying, discriminating, classifying, and quantifying, the imaged objects and/or materials, for example, by analyzing different signature spectra present in pixels of the hyperspectral images.

A high speed hyperspectral imaging system is often required for different types of repeatable and non-repeatable chemical and physical processes taking place during the sub-100 millisecond time scale, which cannot, therefore, be studied using regular hyperspectral imaging techniques. Combustion reactions, impulse spectro-electrochemical experiments, and inelastic polymer deformations, are examples of such processes. Remote sensing of objects in distant scenes from rapidly moving platforms, for example, satellites and airplanes, is another example of a quickly changing observable that is often impossible to repeat, and therefore requires high speed hyperspectral imaging.

Disclosed herein, is a method, and system, for the blending of agricultural products, such as tobacco, via hyperspectral imaging and analysis. In certain forms thereof, provided are methodologies, protocols, procedures and equipment that are highly accurate and highly precise, in that they are reproducible and robust, when evaluating agricultural products, such as tobacco. The testing methodologies disclosed herein exhibit high sensitivity, high resolution, and high speed during automatic on-line operation.

Certain forms disclosed herein are specifically focused on the domain encompassing measuring, analyzing, and determining, micro scale properties, characteristics, features, and parameters of agricultural products, such as tobacco, generally with respect to individual tobacco bales, lots or samples, and specifically with respect to single or individual tobacco leaves contained within the tobacco bales, lots or samples, and more specifically with respect to a wide variety of numerous possible physical, chemical, and/or biological properties, characteristics, features, and parameters of single or individual tobacco leaves contained within a given tobacco bale, lot or sample. In one form, provided is an automatic on-line blending system employing hyperspectral imaging and analysis.

Certain forms disclosed herein use what will be referred to as "hyperspectrally detectable and classifiable codes." As used herein, a "hyperspectrally detectable and classifiable code" is a micro scale property, characteristic, feature, or parameter of a particular bulk agricultural product, such as a tobacco bale, lot or sample, which is hyperspectrally detectable by hyperspectral imaging and analysis in a manner that the resulting hyperspectral data and information, for example, hyperspectral "fingerprint" or "signature" patterns are usable for classifying at least part of a single or individual tobacco leaf contained within that particular tobacco bale, lot or sample. In turn, the classified part of the single or individual tobacco leaf contained within that particular tobacco bale, lot or sample is usable as part of a procedure for blending that particular tobacco bale, lot or sample.

Accordingly, a "hyperspectrally detectable and classifiable code" is defined, generally with respect to a particular individual agricultural product, such as a tobacco bale, lot or sample, and specifically with respect to a single or individual tobacco leaf contained within the particular tobacco bale, and more specifically with respect to a physical, chemical, and/or biological property, characteristic, feature, or parameter, of that single or individual tobacco leaf contained within that particular tobacco bale, lot or sample. The hyperspectrally detectable and classifiable codes are usable as part of a procedure for (uniquely and unambiguously) blending tobacco bales, lots or samples.

Primary examples of micro scale testing for generating hyperspectrally detectable and classifiable codes, include: physical (geometrical/morphological) shape or form and size dimensions of single or individual tobacco leaves; coloring of single or individual tobacco leaves; moisture (water) content of, or within, single or individual tobacco leaves; type, distribution, and compositional make-up, of (organic and inorganic) chemical species or components, of single or individual tobacco leaves; types, distribution, and compositional make-up, of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects, such as exposure to aqueous liquids or to non-aqueous (organic based) liquids; and activity and/or reactivity of single or individual tobacco leaves in response to biological stimuli or effects, such as exposure to biological organisms; physical (geometrical/morphological) shape or form and size dimensions of single or individual tobacco leaves; coloring of single or individual tobacco leaves; moisture content of, or within, single or individual tobacco leaves; types, distribution, and compositional make-up, of (organic and inorganic) chemical species or components, of single or individual tobacco leaves; types, distribution and compositional make-up of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects (such as exposure to aqueous (water based) liquids or to non-aqueous (organic based) liquids); and activity and/or reactivity of single or individual tobacco leaves in response to biological stimuli or effects, such as exposure to biological organisms.

In one form, tracking and accounting for the spatial (i.e., geographical) and temporal (i.e., seasonal) variability or dependency of physical, chemical, and/or biological properties, characteristics, features, and behavior, of agricultural products, such as tobacco bales, lots or samples and tobacco leaves are provided. Such spatial and temporal variability or dependency of tobacco leaves, and therefore, of tobacco bales, lots or samples, can be uniquely and unambiguously tracked and accounted for by use of the hyperspectrally detectable and classifiable codes and can therefore be incorporated into a procedure for (uniquely and unambiguously) blending tobacco bales, lots or samples. It should be understood that the technique could be used for products other than tobacco as well, like tea, fruits while making fruit products, grapes during wine manufacturing, other agricultural products, and the like.

Quality and character of tobacco or other agricultural products such as tobacco vary due to factors such as, for example, particular plant variety, growth region, weather conditions, fertilizer and crop protection agents used, etc. To make a high quality, consistent product, producers blend various agricultural product samples, which also allows for design of a sensorially acceptable product. Sensory attributes of a blend depends upon the components in the blend. The sensory attributes are usually determined by subjective evaluation using product panels. Blending is done by expert blenders who rely on subjective judgment about the raw material available, to develop the blend. Often, it is necessary for the blenders to make a product from the individual raw material, for example, in the case of tobacco, to make cigarettes and other tobacco products from individual tobacco grades, and then use subjective sensory evaluation to determine the blend. Thus, blending can be a time consuming and laborious process, with final result dependent upon the experience and skill of the blenders and subjective evaluation from the sensory panels.

As such, it may be appreciated that a large number of variables impact tobacco blending, with the set of blend criteria including, but not limited to, year of harvest, type of tobacco, leaf location on the tobacco plant, grade, growing region, seasonal weather conditions, etc., as those skilled in the art would plainly recognize.

Figure 2:
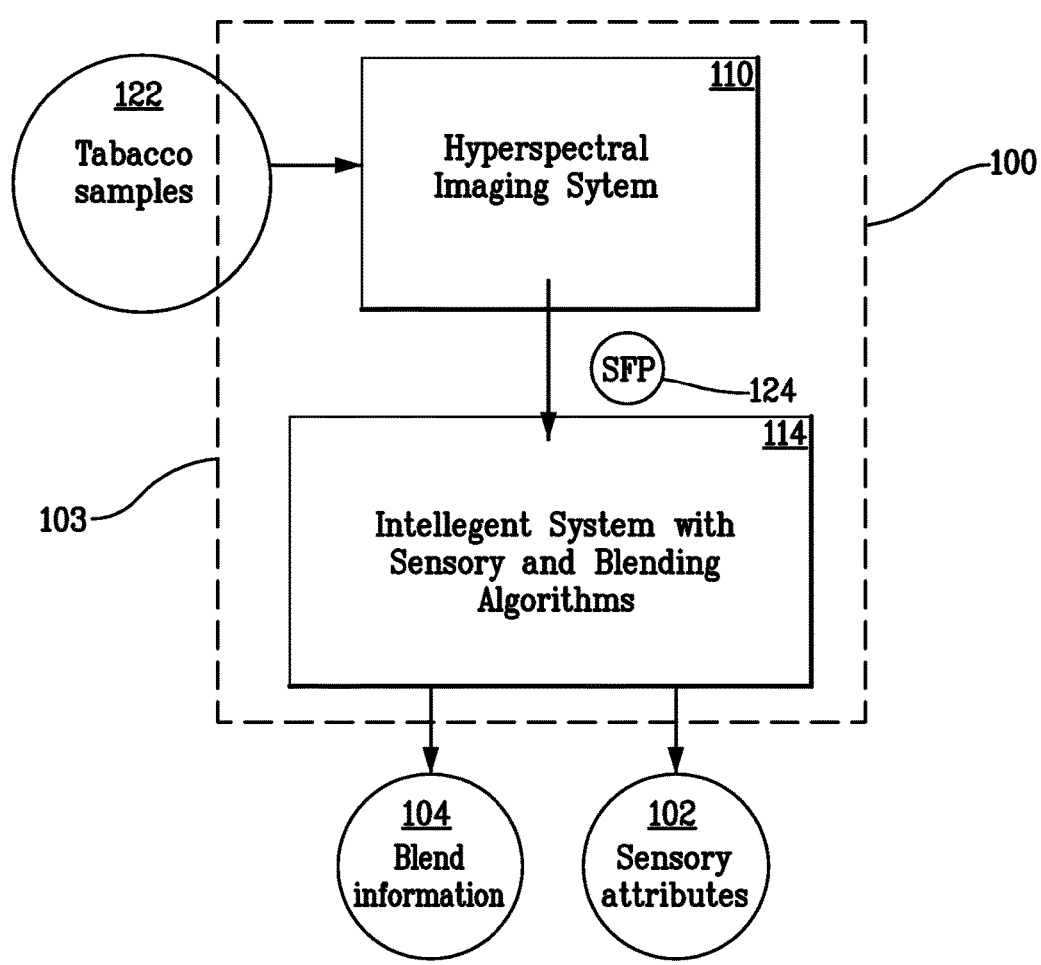
FIG. 2 presents, in block diagram form, a second stage of an automatic blending system, in accordance herewith.

In the following, the invention is described in detail for the case of blending tobacco. However, it should be understood that tobacco is used only to illustrate the methods and systems contemplated herein and not as limiting the application of the methods and systems described herein. Referring to FIGS. 1 and 2, disclosed herein is a blending system 100 to determine the sensory attributes 102, which can be used to form consistent, quality blends 104 based upon available raw materials. The system 100 uses spectral fingerprints 106 and 124 obtained by hyperspectral imaging system 110. Each spectral fingerprint 106 or 124 gives a measure of the physical and chemical characteristics of the tobacco sample 108 or 122 (or other agricultural raw material). The physical and chemical characteristics determine the sensory attributes of the different tobacco samples 108 or 122. By building a database of the spectral fingerprints 106 of different types and grades of tobacco 108 and using blending schemes 112 employed by human blenders, an intelligent system 118 can be built based upon statistical prediction and/or neural network and artificial intelligence techniques 120 to develop an automatic blending system 100. The algorithm can be optimized for cost reduction by including the cost of the different batches of tobacco samples as one of the variables used in the optimization scheme.

Referring to FIG. 1, in a first stage 101 of the system 100, a database is built with the existing tobacco samples 108 and the hyperspectral fingerprints 106 and the subjective sensory attributes 116 for different lots of tobacco samples. An intelligent system 118 is built based upon a neural network or an artificial intelligence algorithm 120 that provides a mapping of the hyperspectral signature with the subjective sensory attributes 116 and evaluation score from expert blenders 120. The costs of individual tobacco lots can also be used as an independent parameter in the algorithm to optimize the blending scheme for sensory attributes and cost effectiveness. At the end of the first stage 101, there is formed a composite hyperspectral signature for one or more acceptable blends, which can be correlated to satisfactory sensory attributes.

Referring to FIG. 2, in a second phase 103, spectral fingerprints 124 of tobacco bales, lots or samples 122 are obtained. The cost of each of these tobacco bales, lots or samples 122 are also obtained and used as an input to the system 100. Intelligent system 114 will determine, using the expert system 118 developed in the first phase 101, the best blending parameters for minimum cost and acceptable sensory attributes using the input parameters, the spectral fingerprints 124, and the cost and availability of tobacco bales, lots or samples.

Accordingly, provided is a method for blending of agricultural product utilizing hyperspectral imaging. At least one region along a sample of agricultural product is scanned using at least one light source of a single or different wavelengths. Hyperspectral images are generated from the at least one region. A spectral fingerprint for the sample of agricultural product is formed from the hyperspectral images. A plurality of samples of agricultural product is blended based on the spectral fingerprints of the samples according to parameters determined by a computer processor executing a blending algorithm.

The method may comprise scanning multiple regions along the sample of agricultural product using at least one light source of a single or different wavelengths; and generating hyperspectral images from the multiple regions. The method may further comprise determining a code for the sample.

The blending may form a blended agricultural product with desirable sensory attributes. The method may further comprise determining one or more features of a spectral fingerprint that corresponds to the desirable sensory attributes. Determining one or more features of a spectral fingerprint that correspond to the desirable sensory attributes may comprise the steps of: (i) scanning at least one region along a sample of a desirable agricultural product using at least one light source of different wavelengths; (ii) generating hyperspectral images from the at least one region; and (iii) forming a spectral fingerprint for the sample of the desirable agricultural product from the hyperspectral images. The desirable agricultural product may be a blended agricultural product blended by a human. The method may further comprise correlating one or more features of the spectral fingerprint for the sample of the desirable agricultural product to the desirable sensory attributes.

The agricultural product may comprise tobacco. The tobacco may be in the form of a bale, lot or sample. At least one light source may be positioned to minimize the angle of incidence of each beam of light with the bale of tobacco.

Cost of the samples may be a factor used by the computer processor in the blending step.

The method may further comprise repeating the steps of scanning at least one region along a sample of agricultural product using at least one light source of different wavelengths, generating hyperspectral images from the at least one region, and forming a spectral fingerprint for the sample of agricultural product from the hyperspectral images, for a plurality of samples of agricultural product prior to blending the plurality of samples of agricultural product. The method may further comprise, prior to the blending step, storing data about the spectral fingerprints of the plurality of samples of agricultural product within a computer storage means, and storing at least a portion of at least some of the plurality of samples of agricultural product; the blending step may comprise blending at least a portion of at least some of the plurality of samples of agricultural product stored in the previous step.

Further provided is a system for blending of agricultural product, according to the methods described above.

Also provided is a method for determining blending parameters for an agricultural product utilizing hyperspectral imaging. Multiple regions along a sample of a desirable agricultural product are scanned using at least one light source of different wavelengths. Hyperspectral images are generated from the multiple regions. A spectral fingerprint is formed for the sample from the hyperspectral images. One or more features of the spectral fingerprint are correlated to desirable sensory attributes of the sample.

The method may further comprise storing data about the spectral fingerprint within a computer storage means, and repeating the steps of scanning multiple regions along a sample of a desirable agricultural product using at least one light source of a single or different wavelengths, generating hyperspectral images from the multiple regions, forming a spectral fingerprint for the sample from the hyperspectral images, storing data about the spectral fingerprint within a computer storage means, using a plurality of desirable agricultural products. The desirable agricultural product may be a blended agricultural product blended by a human.

Additionally provided is a system for determining blending parameters for an agricultural product, according to the methods described above.

Figure 3:
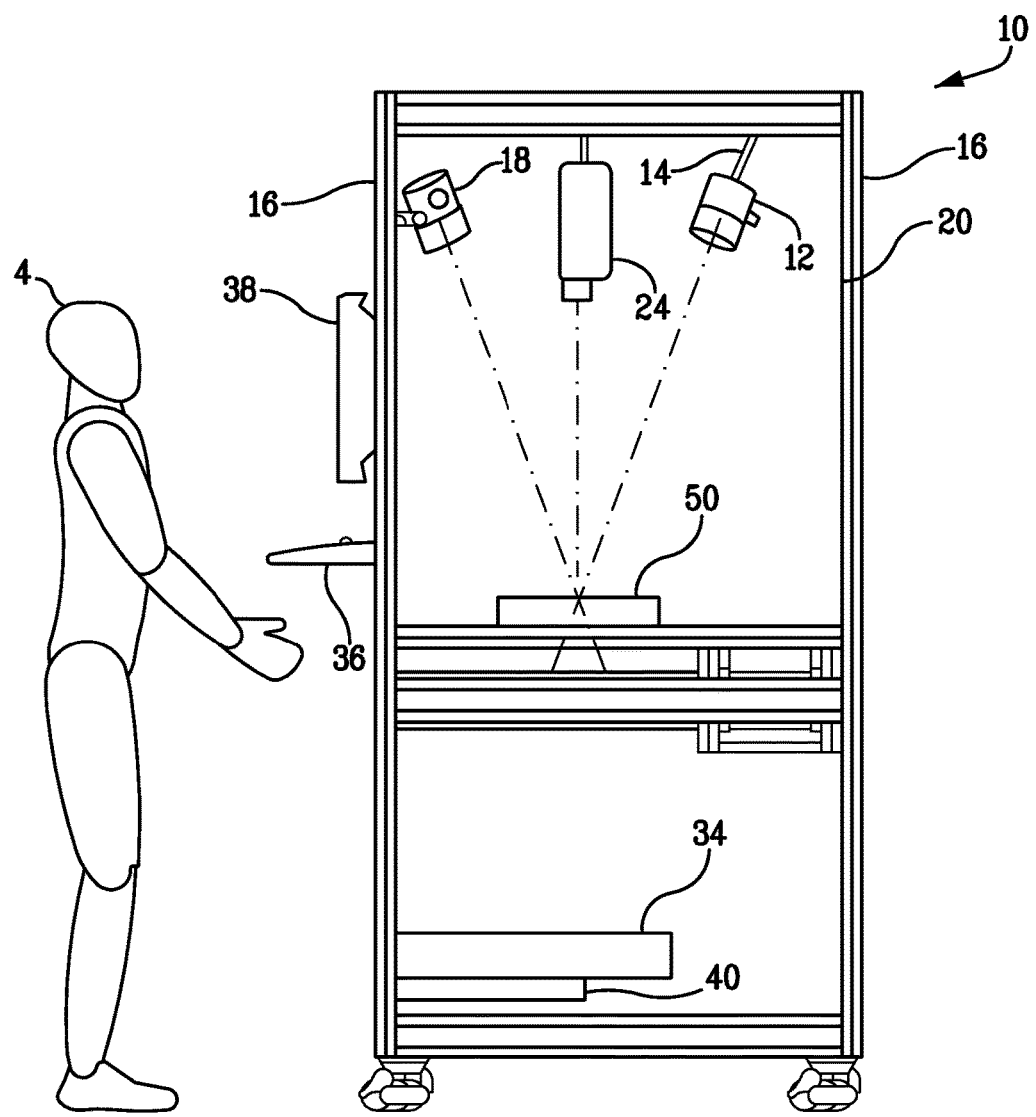
FIG. 3 presents an example of an implementation of a system for scanning an agricultural product employing hyperspectral imaging and analysis, in accordance herewith.

Referring now to FIG. 3, a system 10 for grading an agricultural product P employing hyperspectral imaging and analysis is shown in schematic form. The system 10 includes at least one light source 12 for providing a beam of light. As shown, the at least one light source 12 may be mounted on an arm 14 for positioning at least one light source 12 in proximity to the agricultural product (not shown), which may be positioned on platform 50. In one form, arm 14 is mounted to frame 16 of cabinet 20 and may be either fixed thereto or moveably positionable, as will be described hereinbelow. As shown in FIG. 3, a second light source 18 may also be provided and mounted to frame 16 of cabinet 20 or, optionally, to an arm (not shown), which in turn is mounted to frame 16 of cabinet 20.

In one form, the at least one light source 12 for providing a beam of light of different wavelengths comprises a tungsten, halogen or a xenon light source. In another form, the at least one light source 12 for providing a beam of light comprises a mercury light source. In yet another form, the at least one light source or the second light source 18 comprises an ultraviolet light source for use in providing a chemical signature of the agricultural product P. This optional ultraviolet light source adds an additional media of classification that provides a better understanding of an agricultural product's quality. In still yet another form, the at least one light source 12 comprises a xenon light source, the second light source 18 comprises a mercury light source and a third light source (not shown) comprises an ultraviolet light source.

In one form, the at least one light source 12 and/or the second light source 18 may be positioned to minimize the angle of incidence of a beam of light with the agricultural product P.

In order to segregate ambient light from the light provided by system 10, walls (not shown) may be added to cabinet 20 to form an enclosure to provide a dark-room-like environment for system 10.

The hyperspectral image of a scene or a sample is obtained using hyperspectral imaging camera 24.

Referring still to FIG. 3, a computer 40 having a processor capable of rapidly handling system data is provided and programmed to compare the detected component wavelengths to a database of previously analyzed agricultural products to identify agricultural product P. Computer 40 may be a personal computer having an Intel® Core™2 Quad or other processor. Computer 40 may also control the operation of the system 10 and the positioning of the head unit 20 about agricultural product P. A device 34 for providing an uninterrupted source of power to computer 40 may be provided, such devices readily available from a variety of commercial sources. As is conventional, computer 40 may also include a keyboard 36 and monitor 38 to enable input and system monitoring by a user U. A regulated power supply 34 may be provided to assure that a tightly controlled source of power is supplied to system 10.

Test results are based on the scanning and counting of individual samples, each comprising dozens of scans, and each sample classified using spectral band features, spectral finger prints (SFP), major spectral representative components, purity and quality of each major compound (component, SFP), relative quantity of each SFP and, optionally, crystallization and morphological features.

A plurality of samples of agricultural products, such as tobacco bales, lots or samples are scanned. As indicated, for agricultural products such as tobacco, a significant number of samples should be scanned in order that the impact of sample or lot variability is reduced. In practice, it has been observed that the impact due to this variability can be reduced when the number of samples N is about 25. However, by carefully selecting representative samples, fewer samples could be used to incorporate all the normal variations observed in a particular product lot. Applying this technique to tobacco, tobacco samples may be scanned using xenon and/or mercury and/or tungsten, and/or halogen light sources and an optional ultraviolet light source may be used for chemical signature classification.

In operation, the light source(s) is activated (one, two, three or more spot lights in parallel to the region of interest (ROI)), permitting redundant data to be gathered. A plurality of regions of interest (such as by way of example, but not of limitation, a 20 cm×20 cm area for each ROI) is scanned for each sample to provide one, two, three or more hyperspectral images. Scanning is performed and the reflection spectral grading signature and optional fluorescence spectral chemical signature received. The images are then saved and a database (including labels identifying the particular sample and/or lot) is thus formed from the combined information obtained for the N samples During scanning, the hyperspectral camera system provides a three dimensional hyperspectral image cube. The image cube, which may be, by way of example, but not of limitation, on the order of about a 696 pixel by 520 pixel array. Such a picture or frame would thus contain about 361,920 pixels. As may be appreciated by those skilled in the art, each pixel may contain about 128, 256, 500 or more spectra points at different wavelengths for an agricultural product such as tobacco.

Figure 4:
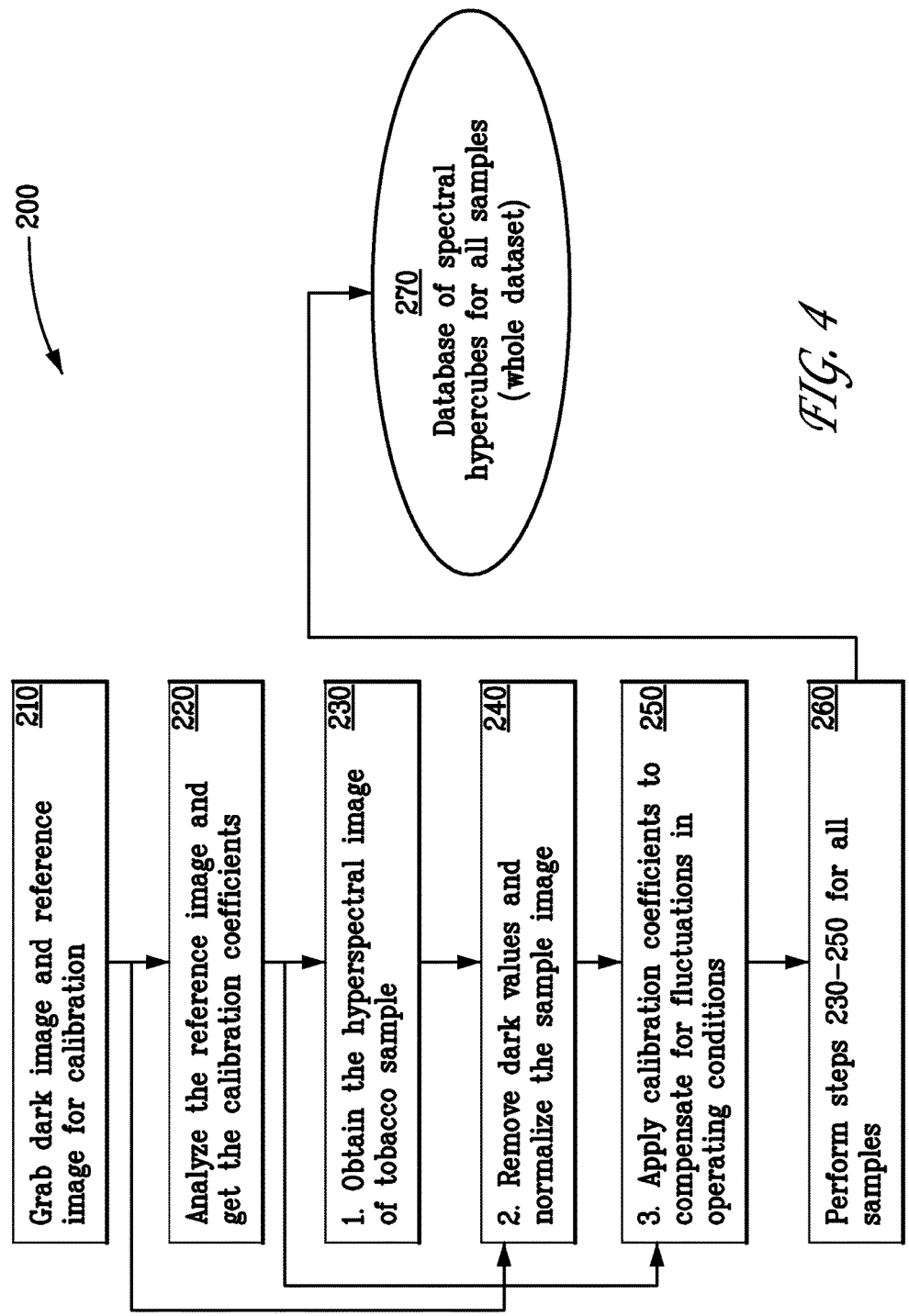
FIG. 4 presents a method for analyzing data to create a spectral library, in accordance herewith.

Referring now to FIG. 4, an algorithm 200 for use in the system and methods described herein will now be disclosed. In step 210, a dark image and reference image are obtained for use in system calibration. In step 220, the reference image is analyzed and calibration coefficients are obtained. In step 230, a hyperspectral image of a tobacco sample is obtained. In step 240, using the information obtained during calibration, dark values are removed and the sample image normalized. In step 250, calibration coefficients are applied to compensate for fluctuations in operating conditions (e.g., light intensity, ambient conditions, etc.). In step 260, steps 230-250 are repeated for all samples and the data so obtained is added in step 270 to the database of spectral hypercubes (whole dataset). It should be understood that the algorithm for creating the database as illustrated in FIG. 4 is referenced to tobacco samples by way of illustration only and not as limiting. The same steps could be used to create the whole spectral database for application in other agricultural products like tea, fruits grapes or other products. The result is 350, a spectral library for all the samples that could be used to form the final product which contains the spectral fingerprints of the dataset found in step 340, and the unique spectra found in step 330.

Figure 5:
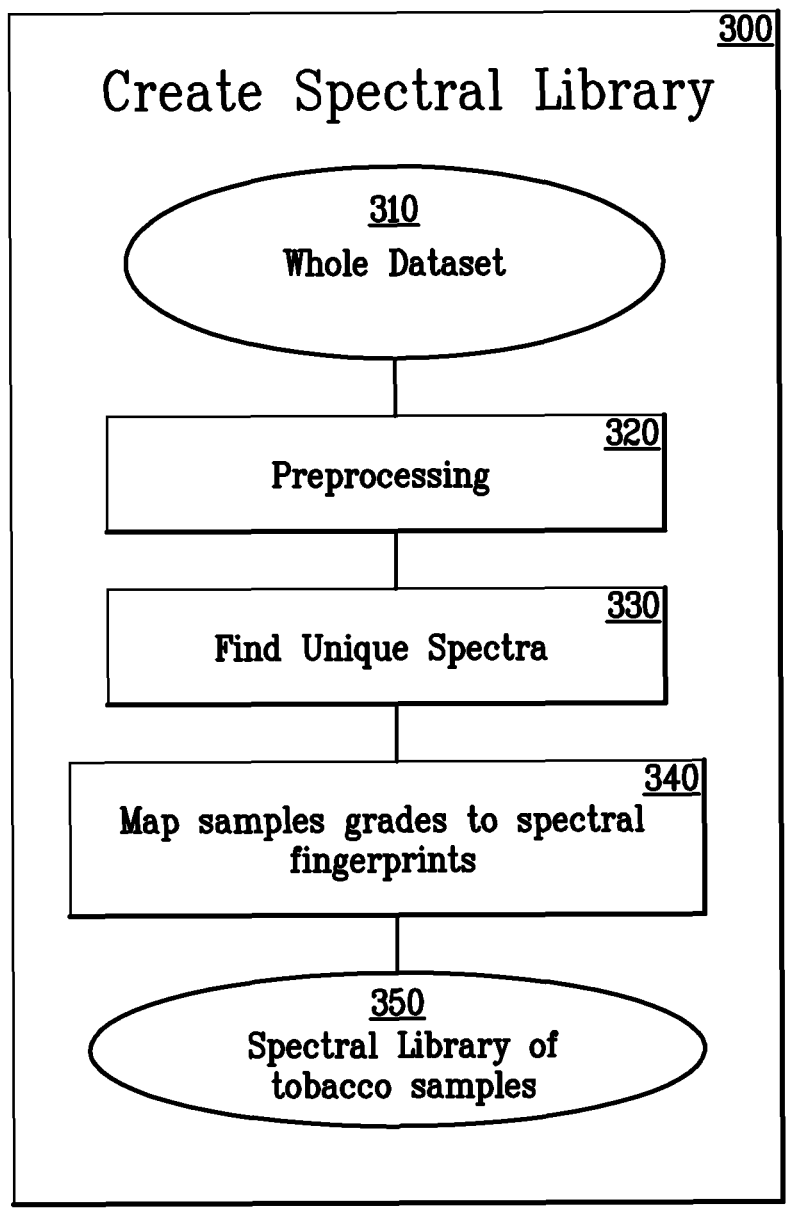
FIG. 5 presents a method for analyzing data to create a spectral library, in accordance herewith.

Referring now to FIG. 5, a method for analyzing data to create a spectral library of samples 300, in accordance herewith is shown. Spectral library 300 is formed by obtaining a dataset in step 310. In step 320, the dataset is preprocessed. Unique spectra, indicative of the dataset, are identified in step 330. In step 340, spectral distributions (spectral fingerprints) are found for each of the samples using the unique spectra found in step 330.

As may be appreciated, the amount of raw data is very large, due to the large number of pixels existing within a particular image cube. A separate spectral is obtained for each pixel. Advantageously, the method disclosed herein identifies a set of characteristic spectra for the whole dataset. The composition of the spectra provides a signature for the sample, with similar samples having similar signatures or fingerprints. Unique spectral fingerprints are then identified for each blend grade.

Figure 6:
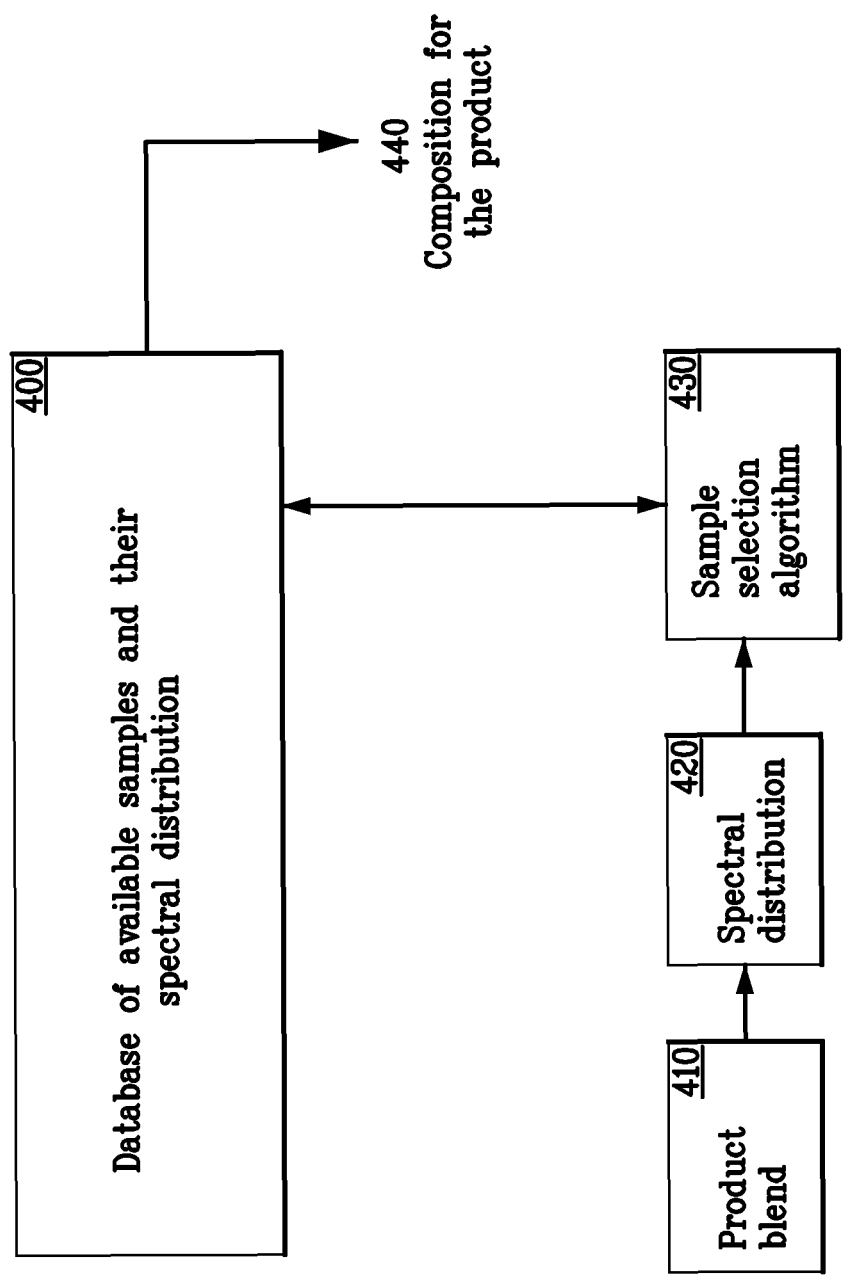
FIG. 6 presents a process for determining the composition of a product based on a database of spectral fingerprints for the samples, in accordance herewith.

Referring now to FIG. 6, a process for using the spectral library or database of the samples developed in FIG. 5 to select the samples to develop a particular product blend is illustrated. Database 400 is the database or spectral library of blending grades developed as illustrated in FIG. 5. In step 410, a product blend is obtained based on either expert evaluation or chemical/sensory attributes. In step 420, a spectral distribution is obtained for the particular product blend of step 410 as disclosed in the foregoing by taking a hyperspectral image and processing the resulting image cube. This spectral distribution provides a signature for the product blend. A product blend selection algorithm is used in step 430, which will provide the necessary composition of the available samples in the sample database for obtaining the desired product blend 410. Step 440 shows the output of the operation, i.e. the composition of the samples in the database to make up the final ingredients for the particular product which will provide the necessary sensory attributes for the product.

Advantageously, the method and system disclosed herein provides a chemical imaging platform that enables speed and exceptionally high sensitivity, thus accurate and non-destructive nature, wherein measurement time is greatly reduced. This enables the tracking of the monitored material with high repeatability.

The method and system disclosed herein provides a highly sensitive hyper spectral imaging analyzer with co-sharing database capabilities. The digitized highly sensitive imaging system disclosed herein enables the imaging of materials components, more detailed observation and provides more specific, sensitive, accurate and repeatable measurements. This may be achieved using advanced image recognition technologies, as well as adaptive and collaborative data bases and statistical and optimization algorithms.

The method and system disclosed herein is capable of characterizing the composition of inorganic, organic, and chemical particulate matter suspended in agricultural products such as tobacco. The instrument scans leaf or other samples, analyses the scanned samples' wavelength signature, performing trends analysis and compares the gathered data to data bases that may, in one form, be continuously updated. The system then generates reports for system users. A remote network may be provided to support the gathering of data for integrated database construction as well as to support remote professional personnel in real time.

Advantageously, the proposed method requires no sample preparation. In operation, linear calibration plots in the ppm range are obtained for mono-component contamination and for simple compound mixtures in this matrix. Non-contact, non-destructive, near real time on-line, automated physico-chemical imaging, classification and analysis of a sample of tobacco leaves or other agricultural products is provided without the need for consumable materials for sample processing. The system operates using algorithms and software packages, together with unique ultra-high resolution optical components and a two-dimensional sample positioning of regions of interest for generating, for example, five dimensional (5D) spectral images of the tobacco sample under analysis.

All or a portion of the devices and subsystems of the exemplary forms can be conveniently implemented using one or more general purpose computer systems, microprocessors, digital signal processors, microcontrollers, and the like, programmed according to the teachings of the exemplary forms disclosed herein, as will be appreciated by those skilled in the computer and software arts.

In view thereof, in one form there is provided a computer program product for facilitating the blending of agricultural products, determining one or more features of a spectral fingerprint that correspond to desirable sensory attributes, and/or determining blending parameters, including one or more computer readable instructions embedded on a tangible computer readable medium and configured to cause one or more computer processors to perform the steps described above and transmitting information relating to the steps described above over a communications link.

Appropriate software can be readily prepared by programmers of ordinary skill based on the teachings of the exemplary forms, as will be appreciated by those skilled in the software art. Further, the devices and subsystems of the exemplary forms can be implemented on the World Wide Web. In addition, the devices and subsystems of the exemplary forms can be implemented by the preparation of application-specific integrated circuits or by interconnecting an appropriate network of conventional component circuits, as will be appreciated by those skilled in the electrical art(s). Thus, the exemplary forms are not limited to any specific combination of hardware circuitry and/or software.

Stored on any one or on a combination of computer readable media, the exemplary forms disclosed herein can include software for controlling the devices and subsystems of the exemplary forms, for driving the devices and subsystems of the exemplary forms, for enabling the devices and subsystems of the exemplary forms to interact with a human user, and the like. Such software can include, but is not limited to, device drivers, firmware, operating systems, development tools, applications software, and the like. Such computer readable media further can include the computer program product of a form disclosed herein for performing all or a portion (if processing is distributed) of the processing performed in implementing the methods disclosed herein. Computer code devices of the exemplary forms disclosed herein can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary forms disclosed herein can be distributed for better performance, reliability, cost, and the like.

As stated above, the devices and subsystems of the exemplary forms can include computer readable medium or memories for holding instructions programmed according to the forms disclosed herein and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

The forms disclosed herein, as illustratively described and exemplified hereinabove, have several beneficial and advantageous aspects, characteristics, and features. The forms disclosed herein successfully address and overcome shortcomings and limitations, and widen the scope, of currently known teachings with respect to the blending of agricultural products such as tobacco bales, lots or samples.

The forms disclosed herein, provide for blending methodologies (protocols, procedures, equipment) for, by way of example, but not of limitation, tobacco bales, lots or samples, which are highly accurate and highly precise (reproducible, robust), during tobacco bale final selection processes. The forms disclosed herein, provide high sensitivity, high resolution, and high speed (fast, at short time scales), during automatic operation, in an optimum and highly efficient (cost effective) commercially applicable manner.

As may be appreciated, the performance of the methods and systems disclosed herein is dependent of the number of regions and samples scanned, image sizes, light sources, filters, light source energy stability, etc.

EXAMPLES

Example 1

The operation of the system and a method of forming a database will now be described by way of this prophetic example.

The system is initiated and the light sources brought up to operating temperature. A dark image and reference image are obtained for system calibration. The reference image is analyzed and calibration coefficients are obtained. A hyperspectral image of a tobacco or other agricultural sample is obtained.

Using the information obtained during the aforementioned calibration, dark values are removed and the sample image normalized. Calibration coefficients are applied to compensate for fluctuations in operating conditions (e.g., light intensity, ambient conditions, etc.). Hyperspectral images for additional tobacco samples are obtained for additional samples of interest and all data so obtained is added to the database of spectral hypercubes (whole dataset).

A spectral library is formed from the database of spectral hypercubes by first preprocessing the data. Unique spectra, indicative of the dataset are identified and samples mapped to the spectral fingerprints so obtained. The unique spectra are then added to a spectral database of blending grades.

Example 2

A method for using the database created, in accordance herewith, will now be described by way of this prophetic example.

When a new product is to be developed, or the components for matching the sensory character of an existing product is to be determined, first, a spectral distribution is obtained for this product based on the teachings of this invention. As described herein, a selection algorithm is used, the results of which provide the composition of the materials necessary to obtain the product.

Upon implementation in accordance with the foregoing teachings, the system will lessen or obviate the need to use sensorial panels in the development of new blends and in the quality control of blends used commercially.

Example 3

The following is provided as an illustrative example in accordance with the above teachings.

In this example, a hypothetical blend of cut filler of a particular brand of a commercial smoking article comprises components A, B and C. It is also contemplated that for each of those components, there are at least three variations or "Lots" (such as three different stalk positions or the like). Accordingly, first component A includes lots A', A" and A'". Likewise for subcomponents B and C. The three components A, B, and C as well as the three variations or lots are provided as a means of illustration only and should not be construed as limiting. Depending upon the product blend and the material used there could be a plurality of components and variations from a few to several dozen.

Referring to FIG. 1, the first step under the example is to establish a library of the "preferred blended attribute" or "P" of a particular blend for brand. In this example the library is constructed by a sensory panel smoking test cigarettes according to a particular blend (i.e., A, B and C) and determining whether the blend meets the "preferred blended attribute". If so, the particular tested blend is hyper-spectral imaged as taught with reference to FIG. 1 to produce a hyper-spectral image that is known to provide the "preferred blended attribute" for the particular brand.

That hyper-spectral image is then subjected to the step of finding its "unique spectra" by resolving the minimum number of spectra components necessary to identify that which was imaged, using information theoretic approaches such as maximum likelihood and/or principal component extraction and other techniques known in the art. Once the "unique spectra" are identified, the parameters of "P" are established and the associated data is stored in an electronic library for future reference. The result might appear like so:

$$P=(0.30-0.32)x+(0.50-0.55)y+(2.0-2.2)z \ldots$$

wherein x, y, z . . . are each members or "spectral elements" of the set comprising the unique spectra and the digits are pixel values (or a range of pixel values) of the respective spectral element. The range of the coefficients specified (like 0.30 to 0.32 for the spectral feature x as given in the foregoing) is obtained by imaging multiple examples of the preferred product blend.

Further to the illustrative example, each lot of the blend subcomponents A, B and C are characterized according to the same member set of "unique spectra". For example, for component A, the "unique spectra" of lots of A may appear like so:

$$A'=0.20x+0.40y+0.40z \ldots$$

$$A''=0.22x+0.38y+0.45z \ldots$$

$$A'''=0.18x+0.39y+0.37z \ldots$$

Each lot of the other blend subcomponents B and C are characterized in the same way:

$$B'=0.70x+0.30y+0.00z \ldots$$

$$B''=0.72x+0.33y+0.05z \ldots$$

$$B'''=0.78x+0.39y+0.03z \ldots$$

and $$C'=0.10x+0.60y+0.030z \ldots$$

$$C''=0.12x+0.65y+0.35z \ldots$$

$$C'''=0.18x+0.62y+0.29z \ldots$$

With the above characterization of P, together with similar characterization of each of the components A, B and C, it is resolvable through optimization techniques and/or iterative solution techniques and other analyses known in the art to resolve what combination (or proportions) of A (A', A", A'''), B (B', B", B''')' and C (C', C", C''') will yield the values established for "P".

Accordingly, as feedstocks of A, B, and C change, those changes can be addressed mathematically to arrive at the same "preferred blended attribute" or P, with lesser reliance on smoking panels and educated guess-work on how to address the changes in feedstock.

It is to be fully understood that certain aspects, characteristics, and features, of the forms disclosed herein, which are illustratively described and presented in the context or format of a plurality of separate forms, may also be illustratively described and presented in any suitable combination or sub-combination in the context or format of a single form. Conversely, various aspects, characteristics, and features, of the forms disclosed herein, which are illustratively described and presented in combination or sub-combination in the context or format of a single form, may also be illustratively described and presented in the context or format of a plurality of separate forms.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art. To the extent that section headings are used, they should not be construed as necessarily limiting.

While the forms disclosed herein have been described in connection with a number of exemplary forms, and implementations, the forms disclosed herein are not so limited, but rather cover various modifications, and equivalent arrangements, which fall within the purview of the present claims.

What is claimed:

1. A method for blending of agricultural product, the method utilizing hyperspectral imaging and comprising:
   (a) scanning at least one region along a sample of agricultural product using at least one light source of a single or different wavelengths;
   (b) generating hyperspectral images from the at least one region;
   (c) determining a spectral fingerprint for the sample of agricultural product from the hyperspectral images;
   (d) repeating steps (a), (b), and (c) for a plurality of samples of agricultural product; and
   (e) blending the plurality of samples of agricultural product together based on the spectral fingerprints of the samples according to parameters determined by a blending algorithm, to yield a blended agricultural product.

2. The method of claim 1, comprising:
   scanning multiple regions along the sample of agricultural product using at least one light source of a single or different wavelengths; and
   generating hyperspectral images from the multiple regions.

3. The method of claim 1, further comprising determining a physicochemical code for the sample.

4. The method of claim 1, wherein the blending forms a blended agricultural product with desirable sensory attributes.

5. The method of claim 4, further comprising determining one or more features of a spectral fingerprint that correspond to the desirable sensory attributes.

6. The method of claim 5, wherein the blended agricultural product with desirable sensory attributes is blended by a computer controlled system.

7. The method of claim 5, wherein the blended agricultural product with desirable sensory attributes is blended manually.

8. The method of claim 5, further comprising:
   correlating one or more features of the spectral fingerprint for the sample of a desirable agricultural product to the desirable sensory attributes.

9. The method of claim 1, wherein the agricultural product comprises tobacco.

10. The method of claim 9, wherein the tobacco is in the form of a bale.

11. The method of claim 10, wherein the at least one light source is positioned to minimize an angle of incidence of each beam of light with the bale of tobacco.

12. The method of claim 1, wherein cost of the samples is a factor used by the blending algorithm in step (e).

13. The method of claim 1, wherein the at least one light source for providing a beam of light comprises a light source selected from the group consisting of a tungsten light source, a halogen light source, a xenon light source, a mercury light source, an ultraviolet light source, and combinations thereof.

14. The method of claim 1, further comprising, prior to step (e):
- storing data about the spectral fingerprints of the plurality of samples of agricultural product within a computer storage means; and
- storing at least a portion of at least some of the plurality of samples of agricultural product;
- wherein step (e) comprises blending at least a portion of at least some of the plurality of samples of agricultural product stored in the step of storing at least a portion of at least some of the plurality of samples of agricultural product.

* * * * *